US009782195B2

(12) United States Patent
Mactaggart et al.

(10) Patent No.: US 9,782,195 B2
(45) Date of Patent: Oct. 10, 2017

(54) FLUID JET ARTERIAL SURGICAL DEVICE

(71) Applicant: Board of Regents of the University of Nebraska, Lincoln, NE (US)

(72) Inventors: Jason N. Mactaggart, Omaha, NE (US); Nicholas Y. Phillips, Omaha, NE (US); Amy R. Mantz, Omaha, NE (US); Alexey Kamenskly, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 301 days.

(21) Appl. No.: 14/548,046

(22) Filed: Nov. 19, 2014

(65) Prior Publication Data
US 2015/0142030 A1    May 21, 2015

Related U.S. Application Data

(60) Provisional application No. 61/906,461, filed on Nov. 20, 2013.

(51) Int. Cl.
*A61B 17/3203* (2006.01)
*A61M 25/09* (2006.01)
*A61B 17/00* (2006.01)

(52) U.S. Cl.
CPC .... *A61B 17/3203* (2013.01); *A61B 17/32037* (2013.01); *A61M 25/09* (2013.01); *A61B 2017/00778* (2013.01)

(58) Field of Classification Search
CPC .......... A61B 17/3203; A61B 17/32037; A61B 2017/00778; A61M 25/09
USPC ....................................................... 600/585
See application file for complete search history.

(56) References Cited

U.S. PATENT DOCUMENTS

| 4,690,672 A | * | 9/1987 | Veltrup .............. A61B 17/3203 604/43 |
| 4,870,953 A | | 10/1989 | DonMicheal et al. |
| 5,135,482 A | * | 8/1992 | Neracher ......... A61B 17/32037 604/22 |

(Continued)

FOREIGN PATENT DOCUMENTS

| WO | WO 96/40476 | 12/1996 |
| WO | WO 99/33510 | 7/1999 |

OTHER PUBLICATIONS

"Endovascular Treatment for Dissection of the Descending Aorta", Jean-Paul Beregi, et al.—The Lancet—vol. 356—Aug. 5, 2000—pp. 482-483.

(Continued)

*Primary Examiner* — Julian W Woo
(74) *Attorney, Agent, or Firm* — Fish & Richardson P.C.

(57) ABSTRACT

A catheter mounted arterial surgical tool has a body with a fluid jet prong extending from a distal end of the body along a prong axis that is parallel to and laterally offset from a body axis. A fluid passage extends through the fluid jet prong to an outlet that points laterally relative to the prong axis. A deflector anvil extends from the distal end of the body along a deflector axis that is parallel to and offset from the body axis. The deflector anvil has a face that faces toward the fluid jet prong and is impinged by a fluid jet discharged from the outlet. A pair of guide wire holes extend from the proximal to the distal end of the body parallel to the body axis for receiving guide wires to enable the body to slide along the guide wires.

20 Claims, 4 Drawing Sheets

(56) References Cited

U.S. PATENT DOCUMENTS

| | | | |
|---|---|---|---|
| 5,304,115 A | 4/1994 | Russell et al. | |
| 5,318,518 A * | 6/1994 | Plechinger | A61B 17/32037 604/22 |
| 5,496,267 A * | 3/1996 | Drasler | A61B 17/32037 604/22 |
| 5,527,330 A * | 6/1996 | Tovey | A61B 17/32037 604/43 |
| 5,827,310 A | 10/1998 | Marin et al. | |
| 5,944,686 A * | 8/1999 | Patterson | A61B 17/3203 604/22 |
| 6,013,076 A | 1/2000 | Goble et al. | |
| 7,115,100 B2 * | 10/2006 | McRury | A61B 10/0266 600/562 |
| 8,062,246 B2 * | 11/2011 | Moutafis | A61B 17/3203 604/22 |
| 8,672,989 B2 * | 3/2014 | Schreck | A61F 2/852 623/1.1 |
| 8,900,179 B2 * | 12/2014 | Jenson | A61B 17/221 604/118 |
| 9,238,122 B2 * | 1/2016 | Malhi | A61M 25/0082 |
| 2006/0069323 A1 | 3/2006 | Elkins et al. | |
| 2014/0012252 A1 | 1/2014 | Bliss et al. | |

OTHER PUBLICATIONS

"Cheese Wire" Fenestration of a Chronic Aortic Dissection Flap for Endovascular Repair of a Contained Aneurysm Rupture, Jun Tashiro, MD, MPH, et al.—Journal of Vascular Surgery—submitted Apr. 16, 2013—pp. 1-3.

"Fenestration Revisited", John A. Elefteriades, MD, et al.—Arch Surg—vol. 125—Jun. 1990—pp. 786-790.

"Aortic Fenestration: A Why, When, and How-to-Guide", George G. Hartnell, FRCR, et al.—Radio Graphics—vol. 25, No. 1—Jan. 2005—pp. 175-189.

"A Novel "Cheese Wire" Technique for Stent Positioning Following Difficult Iliac Artery Subintimal Dissection and Aortic Re-Entry", A.F. Watkinson,—Springer Science & Business Media B.V.— 2009—pp. 781-785.

* cited by examiner

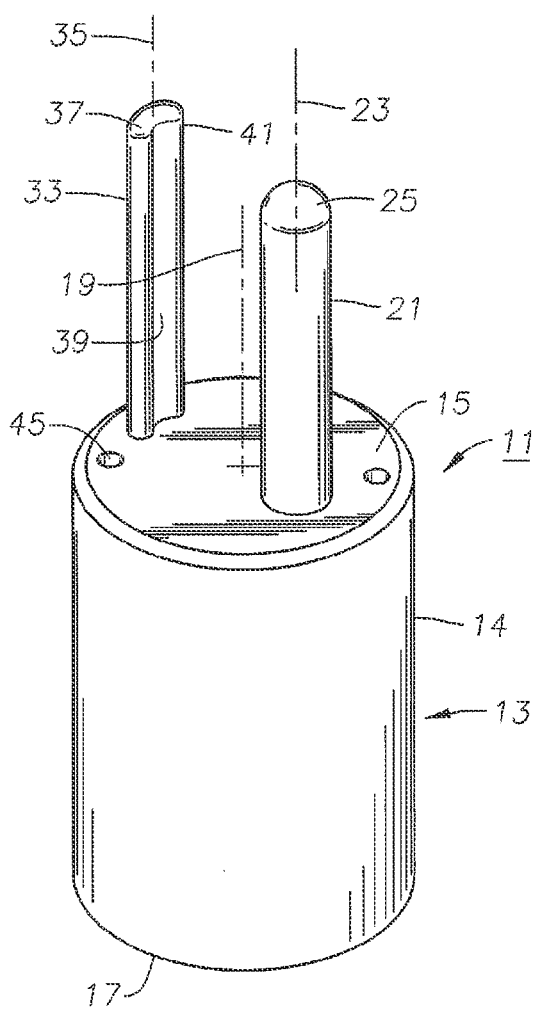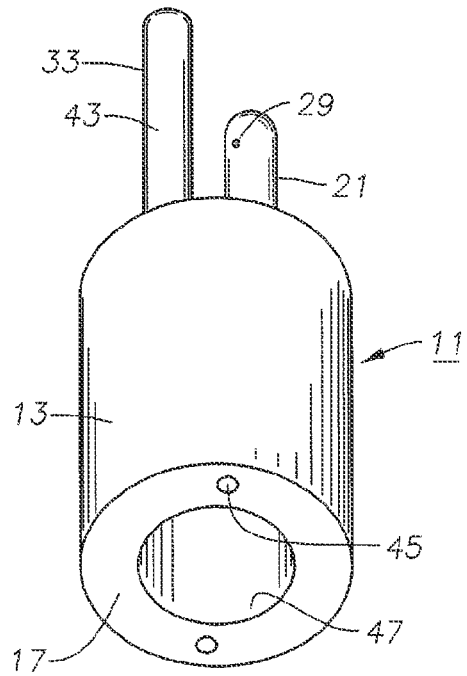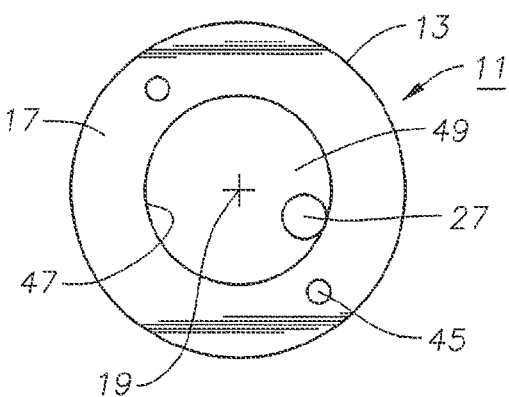
FIG. 1
FIG. 2
FIG. 3

FLUID JET ARTERIAL SURGICAL DEVICE

CROSS REFERENCE TO RELATED APPLICATION

This application claims priority to provisional application Ser. No. 61/906,461, filed Nov. 20, 2013.

FIELD OF THE DISCLOSURE

This disclosure relates in general to a catheter-mounted surgical device that inserts into a vessel, such as an artery or a vein and has a water jet for cutting tissue.

BACKGROUND

Arterial dissection is a deadly disease caused by a tear in the tunica intima of an artery, forming a fake lumen. A thin wall or septum resulting from the tear creates a double barrel portion of the artery, with blood flow on both sides of the septum. The false lumen is on one side of the septum while the true lumen is on the other side. Some arterial dissections can extend up to a meter in length. If untreated, death from rupture or downstream organ ischemia can occur. For patients that survive the initial episode, a chronic dissection occurs and often progresses to an aneurysm with significant aortic rupture risk.

The main surgical method for arterial dissection reconstruction involves open surgical exposure of the artery and associated branch vessels, clamping of the arteries, and then cutting through all three layers of the artery in order to access and repair the dissection. Often the surgeon adds a prosthetic graft to repair the artery wall and re-establish arterial continuity. Clamping arteries and cutting through healthy tissues to repair aortic dissections causes undesired consequences of extra stress placed on the heart with clamping, downstream organ dysfunction from lack of blood flow during clamping, and healthy tissue injury, such as nerve and lung injuries from surgical exposures.

US 2014/0012252 discloses a surgical cutting tool that is inserted into the artery mounted on a catheter. The tool has a blade for cutting a dissection septum. Other tools have been developed for insertion by a catheter into an artery for performing various functions. For example, water jet surgical devices are inserted into arteries on catheters to aspirate and macerate thrombus within an artery.

SUMMARY

The surgical tool disclosed herein has a body with a proximal end, a distal end, and a longitudinal body axis. A fluid jet prong extends from the distal end of the body and has a fluid passage within that leads to an outlet pointing laterally relative to the body axis for delivering a fluid jet. A deflector anvil extends from the lateral distal end of the body directly opposite the jet outlet for contact and dispersal of the fluid jet.

The fluid jet prong and the deflector anvil are positioned such that a straight line extending from the outlet to the deflector anvil passes through the body axis. In the embodiment shown, the outlet points along a line that is generally in a proximal direction and at an acute angle relative to a plane perpendicular to the body axis. The deflector anvil has a face that faces the outlet. In the preferred embodiment, the face has two side edges that are circumferentially apart from each other relative to the body axis. The outlet points along a line that intersects the face of the deflector anvil midway between the side edges. The face may comprise an elongated channel.

The fluid jet prong has a prong axis that is parallel to and offset in a first direction from the body axis. The deflector anvil has a deflector axis that is parallel to and offset from the body axis in a second and opposite direction from the prong axis. The fluid jet prong and the deflector anvil may have lengths that are substantially the same.

A pair of guide wire holes extend through the body from the proximal end to the distal end of the body. A pair of guide wires extend through the holes. The body can slide along the guide wires.

The body has a cavity on the proximal end that is concentric with the body axis. The flow passage in the fluid jet prong joins the cavity. A catheter couples to the body in fluid communication with the cavity for delivering a pressurized fluid to the flow passage.

BRIEF DESCRIPTION OF THE DRAWINGS

So that the manner in which the features, advantages and objects of the disclosure, as well as others which will become apparent, are attained and can be understood in more detail, more particular description of the disclosure briefly summarized above may be had by reference to the embodiment thereof which is illustrated in the appended drawings, which drawings form a part of this specification. It is to be noted, however, that the drawings illustrate only a preferred embodiment of the disclosure and is therefore not to be considered limiting of its scope as the disclosure may admit to other equally effective embodiments.

FIG. 1 is a perspective view of a surgical device in accordance with this disclosure.

FIG. 2 is another perspective view of the surgical device of FIG. 1.

FIG. 3 is a proximal end view of the surgical device of FIG. 1.

DETAILED DESCRIPTION OF THE DISCLOSURE

Figure 4:
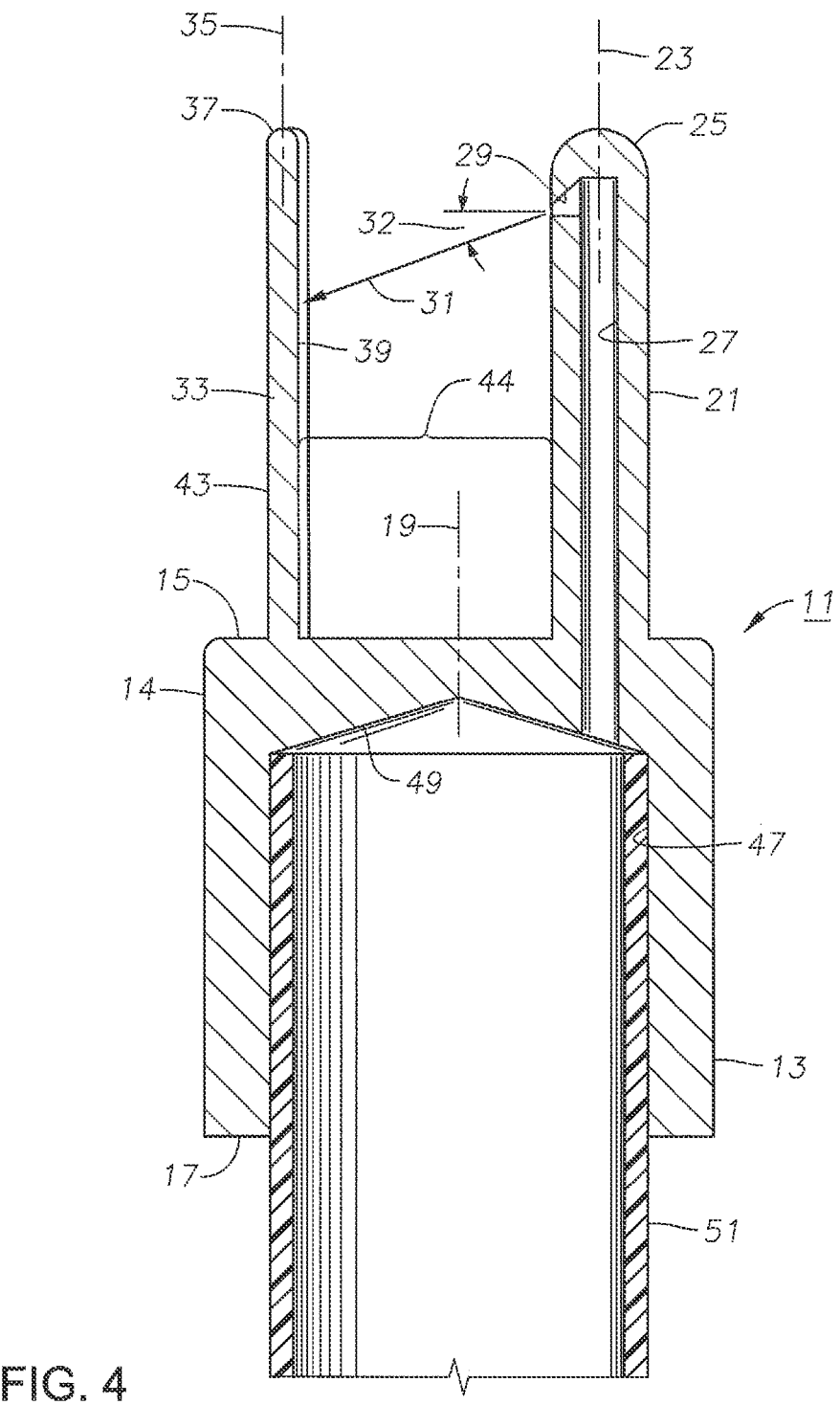
FIG. 4 is an enlarged vertical sectional view of the surgical device of FIG. 1.

The methods and systems of the present disclosure will now be described more fully hereinafter with reference to the accompanying drawings in which embodiments are shown. The methods and systems of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Referring to FIG. 1, surgical tool 11 has a body 13 that preferably has an outer diameter portion 14 that is cylindrical and small enough to be inserted into an artery. Outer diameter portion 14 of body 13 may be approximately 5 mm in diameter or less. Body 13 may also be considered to be a nozzle head or tip. Body 13 has a distal end 15 and a proximal end 17. In this embodiment, distal end 15 and proximal end 17 are located in planes perpendicular to a longitudinal body axis 19 of body 13, but one or both ends 15, 17 could be shaped other than flat.

A fluid jet prong 21 extends from distal end 15 along a prong axis 23 that is parallel with and offset from body axis 19. Fluid jet prong 21 is a rigid member that may be integrally formed with body 13. Fluid jet prong 21 alternately may have an articulating attachment to its distal end. Fluid jet prong 21 has a tip 25 spaced from body distal end 15. Fluid jet prong 21 may be cylindrical, as shown, and tip 25 may be rounded or hemispherical. The outer diameter of fluid jet prong 21 is much smaller than the outer diameter of body outer diameter portion 14. Fluid jet prong 21 may be spaced radially inward from body outer diameter portion 14. In this embodiment, fluid jet prong 21 is closer to body outer diameter portion 14 than to body axis 19. Alternately, the outer side of fluid jet prong 21 could be flush with body outer diameter portion 14.

Referring to FIG. 4, a fluid passage 27 extends within fluid jet prong 21 along prong axis 23. The distal end or termination of fluid passage 27 is a short distance below prong tip 25. An outlet 29 extends radially outward from fluid passage 27 relative to prong axis 23 near prong tip 25. Outlet 29 may be in the shape of a converging nozzle for creating a fluid jet 31 or it may have other shapes. Outlet 29 is aligned to discharge fluid jet 31 laterally along a line passing through body axis 19. Also, outlet 29 may be oriented at an acute angle 32 downward relative to a plane perpendicular to body axis 19. That is, fluid jet 31 points laterally and also generally in a proximal direction. Angle 32 may vary, such as between 15 and 30 degrees, and is illustrated to be about 20 degrees. The diameter of outlet 29 may vary, but it must be quite small for the purpose of repairing a dissection. In one embodiment, the minimum diameter of outlet 29, is 0.1 mm, much smaller than the inner diameter of fluid passage 27. The desired pressure of fluid jet 31 is between 30-100 bar, but it could be higher or lower. Outlet 29 could be other than circular in shape. More than one outlet 29 could be employed. The outlets could have different shapes or sizes, and a sliding sleeve or cover may be incorporated to select which outlet or outlets are desired to discharge the fluid.

Referring again to FIG. 1, a deflector anvil 33, which also might be called an anvil, extends from body distal end 15 along a deflector anvil axis 35. Deflector anvil 33 is a rigid member that may be integrally formed with body 13. Body 13, fluid jet prong 21 and deflector anvil 33 are typically formed from surgical steel, but may be composed of other materials, such as titanium. Deflector anvil 33 has a deflector tip 37 that may be rounded and located the same distance from distal end 15 as fluid prong tip 25. Deflector anvil 33 is not cylindrical in this embodiment; rather it has a face 39 that comprises an elongated concave surface or channel extending from distal end 15 to tip 37. Face 39 faces directly toward fluid jet prong 21, such that fluid jet 31 will impinge face 39. Deflector anvil 33 has two side edges 41 that join face 39 to an outer side 43. Side edges 41 extend along parallel lines from distal end 15 and may be rounded. Outer side 43 may be curved and is shown as a convex segment of a cylindrical surface extending from distal end 15 to deflector tip 37. The radius of outer side 43 may be much smaller than the radius of body outer diameter portion 14. Also, side edges 41 could curve farther back to direct the impinging fluid jet 31 toward a central portion of face 39, further disrupting fluid jet 31.

Figure 7:
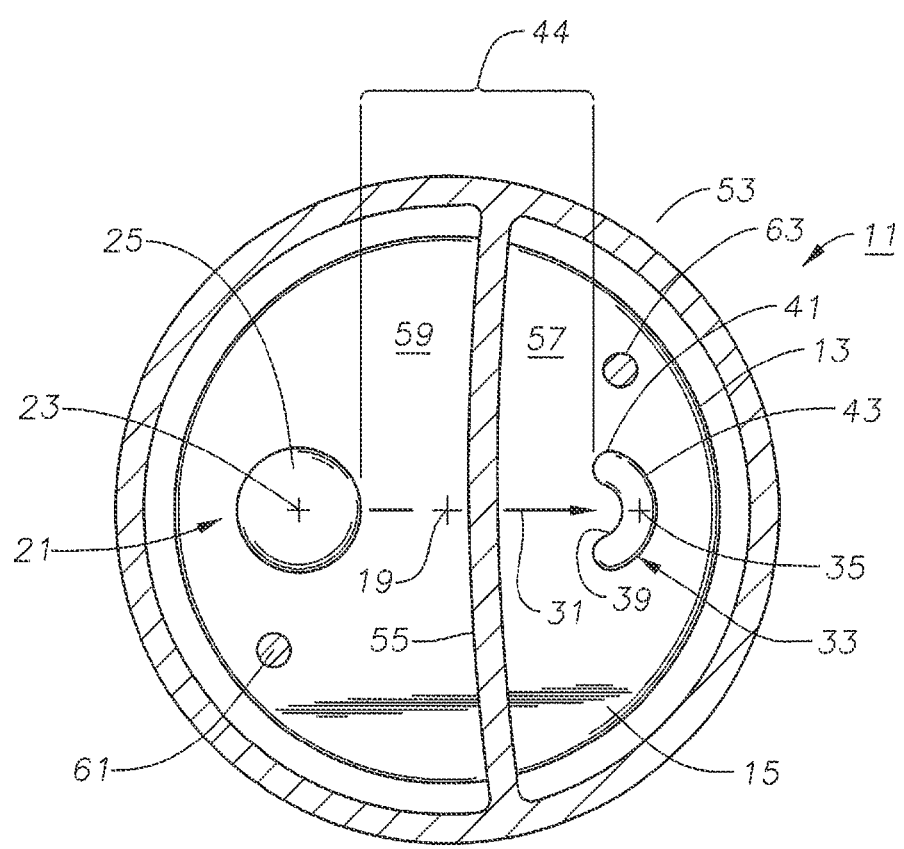
FIG. 7 is another schematic cross-sectional view of the artery illustrated in FIG. 5 and showing the surgical device inserted within.

As shown in FIG. 7, the radius of face 39 and the radius of outer side 43 may have the same center point. The circumferential extent of outer side 43 from one side edge 41 to the other may vary, and in this example is about 110 degrees relative to a center point for the radius of curvature of outer side 43. Deflector face 39 may be smooth or micro-patterned for better diffusion of fluid jet 31

Referring still to FIG. 7, deflector anvil 33 is located on an opposite side of body axis 19 from fluid jet prong 21. Relative to body axis 19, the circumferential distance along body outer diameter portion 14 from deflector anvil 33 to fluid jet prong 21 may be 180 degrees. Preferably, fluid jet 31 passes through body axis 19 and strikes face 39 at a center point between side edges 41. Outer side 43 is spaced radially inward from body outer diameter portion 14 about the same distance as fluid jet prong 21, but outer side 43 could be flush with body outer diameter portion 14. A distance from face 39 to body axis 19 is slightly less than a distance from the inner side of fluid jet prong 21 to body axis 19 in this embodiment.

The space between fluid jet prong 21 and deflector anvil 33 is open from body distal end 15 in a distal direction. The open space creates a linear pathway 44 across surgical tool 11 from one side to an opposite side. Pathway 44 intersects fluid jet 31 at a 90 degree angle. Deflector anvil face 39 bounds one lateral side of pathway 44, and fluid jet prong 21 bounds an opposite side. Body distal end 15 defines a proximal side of pathway 44.

Referring again to FIG. 1, a pair of guide wire holes 45 extend through body 13. Guide wire holes 45 are parallel to each other and to body axis 19. Guide wire holes 45 are spaced radially outward and on opposite sides from body axis 19. Guide wire holes 45 have distal openings at body distal end 15 and proximal openings on body proximal end 17. In this example, guide wire holes 45 are equidistant from body axis 19 and spaced closer to body outer diameter portion 14 than the distance from outer diameter portion 14 to fluid jet prong 21 and deflector anvil 33. Also, as can be observed in FIG. 7, in this example, a straight line extending laterally between guide wire holes 45 will not pass through either fluid jet prong 21 or deflector anvil 33, but it will pass through body axis 19. For example, assume deflector anvil 33 to be at a 90 degree coordinate of body distal end 15 and fluid jet prong 21 to be at a 270 degree coordinate relative to body axis 19. These coordinates places guide wire holes 45 at coordinates of about 45 degrees and 225 degrees.

In an alternative embodiment (not shown), a single guide wire may be used and positioned at a variety of places, including but not limited to body axis 19. In still another embodiment, three or more guide wires may be inserted through three or more guide wire holes in body 13.

Referring again to FIG. 2, body 13 has a cylindrical cavity 47 with an opening at its proximal end 17. Cavity 47 is concentric with body axis 19. As shown in FIG. 3, cavity 47 is a blind hole, having a closed distal end 49 spaced from body proximal end 17. The inlet of fluid passage 27 intersects cavity distal end 49. Since fluid passage 27 is parallel to and offset from body axis 19, the inlet of fluid passage 27 is laterally offset from body axis 19. Referring again to FIG. 4, cavity distal end 49 is shown as being conical with an apex on body axis 19; however, cavity distal end 49 could be flat or slanted from the left side, as shown in FIG. 4 to the opening for flow passage 27.

FIG. 4 also shows a catheter 51 in fluid communication with cavity 47. Catheter 51 comprises conventional flexible medical tubing. In this example, catheter 51 inserts into cavity 47. and an adhesive or mechanical bonds link an outer side of catheter 51 to the inner diameter of the cylindrical portion of cavity 47. Alternately, the outer diameter of the proximal portion of body 13 containing cavity 47 could be smaller, in which case catheter 51 could insert over this smaller outer diameter portion.

Figure 5:
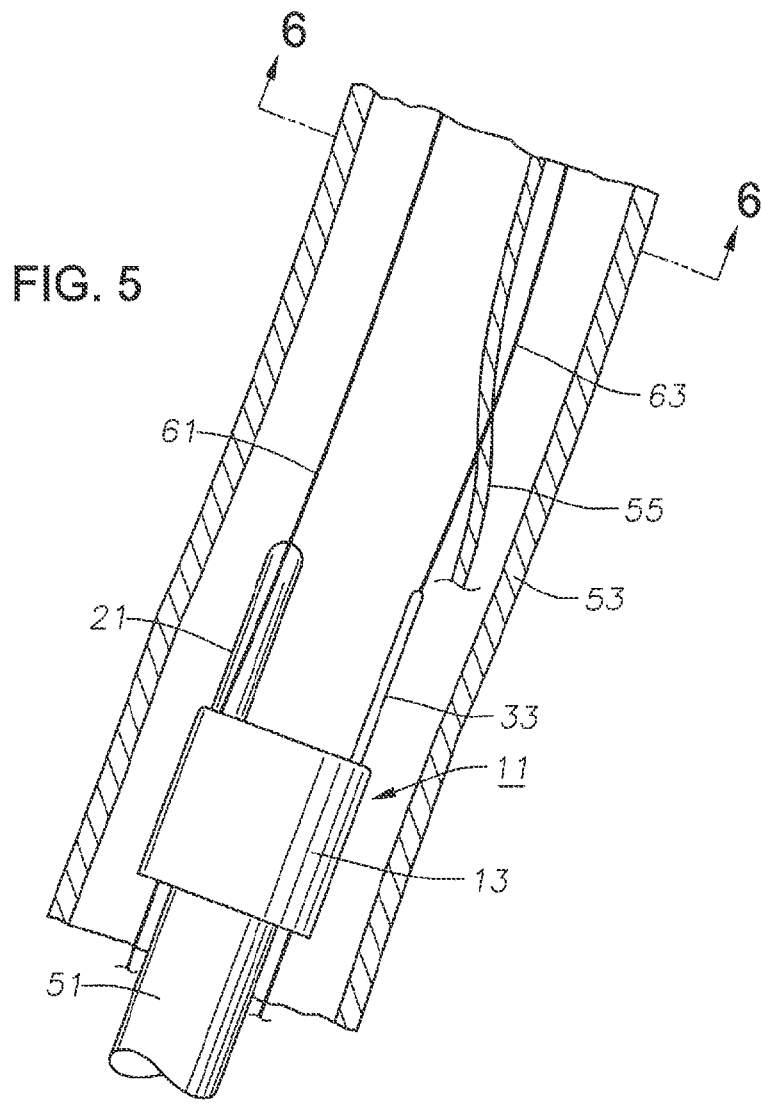
FIG. 5 is a schematic view of the surgical device of FIG. 1 employed to repair an artery having an arterial dissection.
Figure 6:
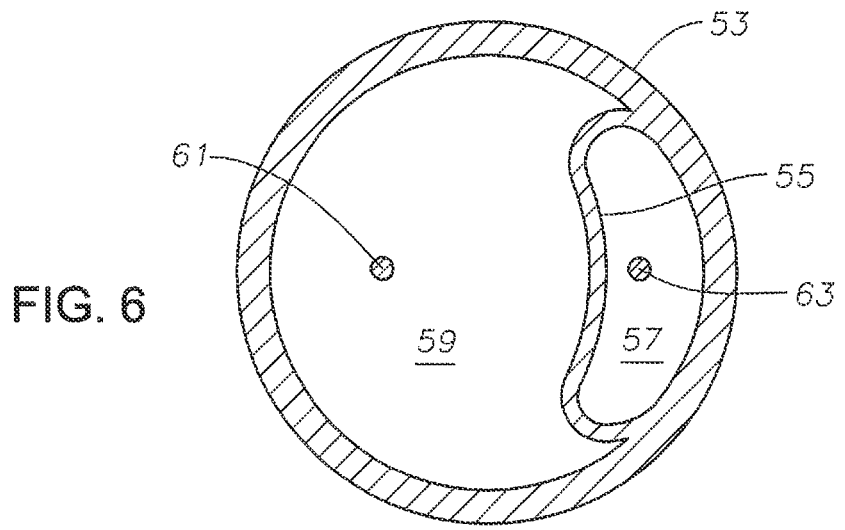
FIG. 6 is schematic cross-sectional view of the artery illustrated in FIG. 5, taken along the line 6-6 of FIG. 5.

FIGS. 5-7 illustrate one use of surgical tool 11. An artery 53 of a patient has developed a dissection, creating a septum 55, which is a thin flexible wall of tissue. Septum 55 has separated from the main wall of artery 53, creating on one side what may be considered to be a false lumen 57. A true lumen 59 exists on the opposite side of septum 55. As shown in FIG. 6, false lumen 57 can create a separate cavity or passage within artery 53 through which blood can enter. The purpose of surgical tool 11 is to form a cut along the length of septum 55.

To cut septum 55, a surgeon first installs guide wires 61 and 63 in artery 53 using conventional techniques, normally including imaging techniques, such as x-ray. The surgeon pushes guide wire 61 through true lumen 59 to a point in the patient's aorta where the distal end of guide wire 61 frictionally secures. The surgeon pushes guide wire 63 through artery 53 until it reaches septum 55. The surgeon manipulates guide wire 63 to cause it to pierce septum 55 and extend up false lumen 57 to a point in the aorta where the distal end of guide wire 63 will frictionally adhere.

The surgeon then inserts surgical tool 11 into artery 53, pushing it upward along with catheter 51. Preferably guide wire 63 will be located close to deflector anvil 33, and guide wire 61 close to fluid jet prong 21. As the surgeon pushes surgical tool 11 further into artery 53, body 13 will slide along guide wires 61, 63, which remain fixed. When surgical tool 11 reaches septum 55, guide wire 63 will cause deflector anvil 33 to push through the pierced opening in septum 55 through which wire 63 passes. Deflector anvil 33 thus enters false lumen 57 while guide wire 61 will cause fluid jet prong 21 to remain in true lumen 59. FIG. 7 illustrates this position, showing septum 55 to be located along pathway 44.

Figure 8:
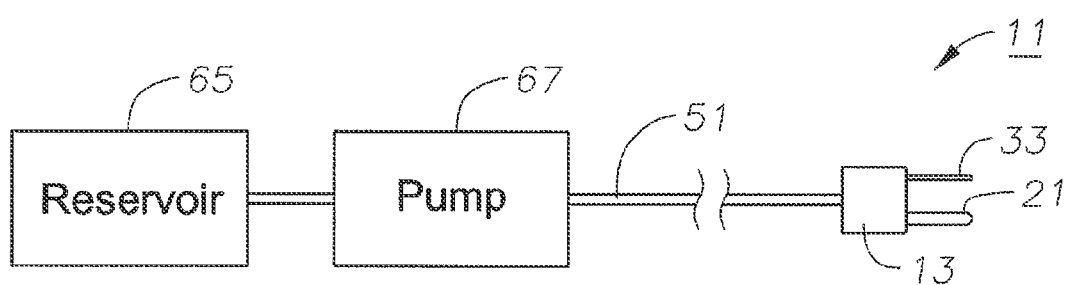
FIG. 8 is a schematic view of the surgical device coupled to a pump and reservoir for delivering high pressure fluid.

Operating personnel will connect a pump 67 to catheter 51, as illustrated in FIG. 8. Pump 67 must be capable of providing adequate pressure to flow passage 27 (FIG. 4) to create a jet 31 that will form a cut in septum 55. Pump 67 for example may be an axial piston pump. Pump 67 draws a fluid, preferably a saline solution of water, from a reservoir 65. The fluid solution could also contain particulate matter to assist cutting efficiency. Pump 67 will pump the fluid through catheter 51 and flow passage 27 (FIG. 4) to outlet 29. Outlet 29 creates high pressure jet 31, which has enough velocity and pressure to cut septum 55 (FIG. 7). Fluid jet 31 impinges on deflector anvil 33 after cutting through septum 55. Deflector anvil 33 prevents the high pressure jet 31 from damaging the opposite wall of artery 53 in true lumen 59. As fluid jet 31 cuts septum 55, the surgeon begins again to advance surgical tool 11 linearly along guide wires 61, 63. Fluid jet 31 cuts through septum 55 along a linear path as surgical tool 11 advances.

When reaching a distal end of septum 55, pump 67 will be stopped. The surgeon then pulls surgical tool 11, including catheter 51, from artery 53. The surgeon may then perform various remedial procedures, such as installing a stent graft to push the remaining flap portions of septum 55 out of a central area of aorta 53 and reconstruct the aorta. Guide wires 61, 63 will be retrieved either before or after the remedial procedures.

Surgical tool 11 may also be employed to cut out an existing stent previously installed within an artery. One guide wire would extend through the stent lumen. Another guide wire would pierce the artery or vessel, extend outside the stent wall, then back into the artery. A third wire (not shown) can pass through the artery inside or outside of the stent to seal a stent graft proximally and distally to a proposed line of cut in the artery wall. The surgical tool cuts the wall and stent after the area is sealed of by the stent graft.

Surgical tool 11 thus enables repair of an arterial dissection without conventional surgery. Other arterial procedures may be performed, as well. Various modifications may be made to the surgical tool.

The invention claimed is:

1. A catheter mounted intra-vascular surgical tool, comprising:
    a catheter defining a longitudinal catheter lumen and a distal tip;
    a body having a proximal end, a distal end, and a longitudinal body axis, the body defining a cavity extending from the proximal end of the body toward the distal end of the body, the cavity configured to receive and surround the distal tip of the catheter to couple the body to the catheter, the body defining a single opening at a distal end of the cavity, the body sized for insertion in a blood vessel using the catheter;
    a fluid jet prong extending from the distal end of the body along a prong axis that is parallel to and laterally offset from the body axis, the fluid jet prong defining a fluid passage in fluid communication with the cavity and with the catheter lumen while the body is coupled to the catheter, the fluid passage extending from the opening defined by the body at the distal end of the cavity, the fluid passage extending axially along the fluid jet prong to an outlet adjacent a distal end of the fluid jet prong, the outlet pointing laterally relative to the prong axis for delivering a fluid jet laterally from the fluid jet prong; and
    a deflector anvil extending from the distal end of the body along a deflector anvil axis that is parallel to and offset from the body axis, the deflector anvil having a face that faces toward the fluid jet prong for impingement by the fluid jet,
    the body defining a pair of guide wire holes extending longitudinally through the body from proximal openings at the proximal end of the body to distal openings at the distal end of the body, the proximal openings spaced radially outward of the cavity, the pair of guide wire holes configured to receive guide wires to enable the body to be slidably guided within the blood vessel along the guide wires.

2. The tool accordingly to claim 1, wherein the prong axis and the deflector anvil axis are parallel linear axes that extend along entire lengths of the fluid jet prong and the deflector anvil respectively.

3. The tool according to claim 1, wherein the fluid jet prong and the deflector anvil are positioned such that a straight line extending from the outlet to the deflector anvil passes through the body axis.

4. The tool according to claim 1, wherein the outlet points along a line that is generally in a proximal direction and at an acute angle relative to a plane perpendicular to the body axis.

5. The tool according to claim 1, wherein the deflector anvil has a face that faces the outlet, the face having two side edges that are circumferentially apart from each other relative to the body axis, and wherein the outlet points along a line that intersects the face of the deflector anvil midway between the side edges.

6. The tool according to claim 1, wherein the deflector anvil has a face that faces the outlet, the face comprising an elongated channel.

7. The tool according to claim 1, wherein the prong axis is offset in a first direction from the body axis, and wherein the deflector anvil axis is offset from the body axis in a second and opposite direction from the prong axis.

8. The tool according to claim 1, wherein the fluid jet prong and the deflector anvil have lengths that are substantially the same.

9. The tool according to claim 1, wherein each of the guide wire holes extends through the body parallel to the body axis.

10. The tool according to claim 1, wherein the body has an overall outer diameter that is five millimeters or less.

11. The tool according to claim 1, wherein:
the distal end of the body has an outer diameter portion coaxial with the body axis; and
the prong axis and the deflector anvil axis are closer to the outer diameter portion than to the body axis.

12. The tool according to claim 1, wherein:
a lateral pathway extends through the body axis between the fluid jet prong and the deflector anvil for positioning a flexible wall between the fluid jet prong and the deflector anvil so that the fluid jet can sever the wall;
the lateral pathway is bordered on one lateral side by the face of the deflector anvil on an opposite lateral side by the fluid jet prong; and
the lateral pathway has a proximal side bordered by the distal end of the body.

13. The tool according to claim 1, wherein:
the face of the deflector anvil comprises an elongated open channel extending parallel with the deflector anvil axis.

14. The tool according to claim 1, wherein the fluid jet prong is configured for delivering the fluid jet along an acute angle relative to a plane perpendicular to the prong axis and generally in a proximal direction.

15. The tool according to claim 1, further comprising a pump coupleable to the catheter for delivering a pressurized fluid to the fluid passage of the fluid jet prong via the catheter lumen.

16. A method of severing a blood vessel wall tissue within a blood vessel, the method comprising:
(a) inserting a catheter mounted intra-vascular surgical tool into the blood vessel over one or more guide wires in the blood vessel, the tool comprising: (i) a body, (ii) a fluid jet prong extending from a first end of the body and having a fluid passage within that has an outlet pointing laterally relative to a body axis of the body, and (iii) a deflector anvil extending from the first end of the body and positioned laterally from the outlet;
(b) positioning the tool so that a portion of the blood vessel wall tissue within the blood vessel is between the fluid jet prong and the deflector anvil; and
(c) cutting the blood vessel wall tissue within the blood vessel by pumping a fluid through the fluid passage and out the outlet, creating a fluid jet that cuts the blood vessel wall tissue within the blood vessel, the fluid jet impinging against the deflector anvil after passing through the blood vessel wall tissue within the blood vessel.

17. The method according to claim 16, wherein step (c) further comprises;
advancing the tool along the blood vessel such that the fluid jet creates a cut linearly along the blood vessel wall tissue within the blood vessel.

18. The method according to claim 16, wherein:
the body defines one or more guide wire holes;
step (a) further comprises inserting each of the one or more guide wires through a respective one of the one or more guide wire holes; and
step (b) further comprises moving the body along the one or more guide wires.

19. The method according to claim 16, wherein:
step (a) further comprises attaching a flexible tube to the body; and
wherein the fluid is pumped through the tube and then through the fluid passage.

20. The method according to claim 16, wherein:
step (c) comprises directing the fluid jet at an acute angle relative to a plane perpendicular to the body axis.

* * * * *

UNITED STATES PATENT AND TRADEMARK OFFICE
CERTIFICATE OF CORRECTION

PATENT NO. : 9,782,195 B2  
APPLICATION NO. : 14/548046  
DATED : October 10, 2017  
INVENTOR(S) : Jason N. MacTaggart et al.

Page 1 of 1

It is certified that error appears in the above-identified patent and that said Letters Patent is hereby corrected as shown below:

On the Title Page

Column 1, item (72) Inventors: Line 7-8, please delete "Alexey Kamenskly, Omaha, NE (US)" and insert -- Alexey Kamenskiy, Omaha, NE (US) --; thereof;

In the Claims

Column 6, Line 60 (Claim 2), please delete "accordingly" and insert -- according --; thereof.

Signed and Sealed this  
First Day of May, 2018

Andrei Iancu  
*Director of the United States Patent and Trademark Office*